United States Patent
Nathan et al.

(10) Patent No.: US 10,471,116 B2
(45) Date of Patent: Nov. 12, 2019

(54) BOTANICAL FORMULATION FOR TREATING SICKLE CELL DISEASE

(71) Applicant: Robert Swift, Fort Collins, CO (US)

(72) Inventors: Swami Nathan, Piscataway, NJ (US); Robert Swift, Fort Collins, CO (US)

(73) Assignee: Robert Swift, Fort Collins, CO (US)

( * ) Notice: Subject to any disclaimer, the term of this patent is extended or adjusted under 35 U.S.C. 154(b) by 0 days.

(21) Appl. No.: 15/899,077

(22) Filed: Feb. 19, 2018

(65) Prior Publication Data

US 2018/0169174 A1   Jun. 21, 2018

Related U.S. Application Data

(63) Continuation of application No. 12/798,524, filed on Apr. 6, 2010, now abandoned.

(51) Int. Cl.
*A61K 36/899* (2006.01)

(52) U.S. Cl.
CPC .................... *A61K 36/899* (2013.01)

(58) Field of Classification Search
None
See application file for complete search history.

(56) References Cited

U.S. PATENT DOCUMENTS 5,800,819 A * 9/1998 Wambebe .............. A61K 33/00
                                                        424/734
6,669,979 B1   12/2003 Zhao et al.

OTHER PUBLICATIONS

Whelan et al., Enzymatic Fractionation of Carbon Isotopes by Phosphoenolpyruvate Carboxylase from C4 Plants, 1973, Plant Physiol, 51: 1051-1054.*
Janssen et al., "Natural Toxins", Food Safety and Toxicity, ed John de Vries, Ph.D.; Ch. 2, 6 pgs. (1997).
Kojima et al., "Tissue Distributions of Dhurrin and of Enzymes Involved in its Metabolism in Leaves of Sorghum bicolor", Plant Physiol.; 63:1022-1028 (1979).
Benedict et al., "Fractionation of the Stable Isotopes of Inorganic Carbon by Seagrasses"; Plant Physiol., 65:512-517 (1980).
International Search Report and Written Opinion dated Jul. 5, 2011, from corresponding International patent application No. PCT/US2011/031051.
Iyamu et al., "In vitro effects of NIPRISAN (Nix-0699): a naturally occurring, potent antisickling agent"; British J of Hematology, 118:337-343 (2002).
Mojisola et al., "Antisickling properties of the fermented mixture of Carica papaya Linn and *Sorghum bicolor* (L.) Moench"; African J of Pharmacy and Pharmacology, 3(4):140-143 (Jan. 1, 2009).
Obodozie et al., "Standardization of the components of niprisan: A phytomedicine for treating sickle cell disease"; J of Medicinal Plant Research, 3(4):284-289 (Jan. 1, 2009).
Castro et al., "Improvement of Sickle Cell Anemia by Iron-Limited Erythropoiesis," American Journal of Hematology, 47:74-81 (1994).
Koduri, "Iron in Sickle Cell Disease: A Review Why Less is Better," American Journal of Hematology, 73:59-63 (2003).
Whelan et al., Enzymatic fractionation of carbon isotopes by phosphoenolypyruvate carboxylase from C4 Plats, 1973, Plant Physiol, 51: 1051-1054.
Oladiji et al., "Anti-anaemic potentials of aqueous extract of *sorghum bicolor* (L.) moench stem bark in rats", 2007, J Ethnopharmacology, 111: 651-656.
Nwinyi et al., "Evaluation of toxicity profile of leaf base extract of sorghum bicolor in rat", Jan. 2009, African J Biotechnology, 8: 334-342.
Nathan et al., "Nicosan: Phytomedicinal Treatment for Sickle Cell Disease"; African Natural Plant Products: New Discoveries and Challenges in Chemistry and Quality. Dec. 20, 2009, 263-276.
Office Action dated May 18, 2016 in corresponding EP Application 11714476.6, 5 pages total.
Wambebe et al., "Efficacy of Niprisan in the prophylactic management of patients with sickle cell disease," Current Therapeutic Research, vol. 62, No. 1, Jan. 2001, pp. 26-34.
Declaration of Robert Swift under 37 C.F.R. § 1.132 filed in U.S. Appl. No. 12/798,524, dated Nov. 21, 2014, 6 pages total.
Office Action dated Jun. 22, 2018 in corresponding Indian Application No. 3125/KOLNP/2012, 8 pages total.
Ameh et al., "Traditional Herbal Management of Sickle Cell Anemia: Lessons from Nigeria", Anemia, vol. 2012, 2012, 9 pages total.

* cited by examiner

*Primary Examiner* — Terry A McKelvey
*Assistant Examiner* — Catheryne Chen
(74) *Attorney, Agent, or Firm* — Merchant & Gould, P.C.

(57) ABSTRACT

An improved plant medicament composition, comprising an extract of *Sorghum bicolor* plant material for treating sickle cell disease is described. A method for the preparation of said composition having the property of inhibiting sickle cells is also provided.

9 Claims, No Drawings

BOTANICAL FORMULATION FOR TREATING SICKLE CELL DISEASE

CROSS-REFERENCE TO RELATED APPLICATIONS

This application is a Continuation Application of prior U.S. patent application Ser. No. 12/798,524, filed Apr. 6, 2010, which is incorporated by reference herein in its entirety.

FIELD OF THE INVENTION

The present invention relates to the field of botanical formulations, botanical compositions and botanical extracts, particularly as it relates to the phytodrug, prodrug or plant medicament for the treatment and management of sickle cell disease and methods of preparing and using same.

BACKGROUND OF THE INVENTION

Sickle cell disease (SCD) is a hereditary blood disorder, affecting over 75,000 people in the United States. Sickle cell disease (SCD) affects over twenty million people throughout the world and is particularly common among those whose ancestors come from sub-Saharan Africa, Spanish-speaking regions in the Western Hemisphere (South America, the Caribbean, and Central America), Saudi Arabia, India, and Mediterranean countries such as Turkey, Greece, and Italy.

In the US, those with SCD have an average mortality in their 40s, a poor quality of life and high medical costs. In SCD, a mutation in .beta.-globin (glu6val) causes deoxygenated sickle hemoglobin (deoxy-HbS) to form insoluble polymers inside red blood cells (RBCs), which deforms the RBCs into rigid shapes or sickle cells that occlude capillaries and small blood vessels. The only disease-modifying drug approved for use in SCD patients is hydroxyurea, an anti-cancer drug. Not all patients respond to hydroxyurea, and it can be poorly tolerated causing myelosuppression in some patients. Despite extensive studies on SCD by researchers over several decades, there has been little progress in the development of additional disease modifying agents. Therefore, new, safer and more effective therapeutic anti-sickling agents are needed to treat patients with SCD, particularly children, which could improve the quality of life, increase the life expectancies of sufferers of this disease, and reduce the estimated 100,000 hospitalizations and $500 million in direct hospital costs due to sickle cell disease in the United States. Sickle cell disease occurs in about 1 in every 500 African American births, and about 1 in 12 African Americans has sickle cell trait. The morbidity and mortality factors associated with sickle cell disease are well known and the acute and chronic trauma of the painful episodes is indescribable. In view of these realities, there is a desperate need for drugs or agents that could alleviate and mitigate the effects of this terrible disease.

U.S. Pat. No. 5,800,819 describes a composition requiring extracts from at least four plant materials for treating sickle cell disease. U.S. Pat. No. 5,800,819 does not describe *Sorghum bicolor*, per se, having anti-sickling activity nor measure the anti-sickling activity of *Sorghum bicolor*. It only describes the anti-sickling activity of the four ingredients mixed together. The present invention provides a distinctly different and improved plant formulation using *Sorghum bicolor* plant material, per se, that shows potent anti-sickling activity against human sickle cells and is simpler to formulate.

SUMMARY OF INVENTION

It is an object of this invention to provide an improved and efficacious botanical medicament for the treatment and management of sickle cell disease.

It is an additional object of this invention to provide a method for the preparation of an improved plant formulation and preparation for the treatment and management of sickle cell disease.

Various other objects and advantages of the invention will become obvious from the detailed description of the invention.

DETAILED DESCRIPTION OF THE INVENTION

Various objects and advantages of the invention are achieved by preparing a botanical formulation comprising an extraction obtained from *Sorghum bicolor* plant, without the use of, or extraction from, any other plant, said extraction from *Sorghum bicolor* plant being effective against sickle cell disease. The *Sorghum bicolor* plant, alone, has not been previously shown to contain anti-sickling activity or anti-sickling compounds. The formulation could be administered in any suitable form such as a tablet, capsule, suspension, solution, powder, and the like, to treat sickle cell disease and may further comprise any pharmaceutically acceptable carrier and excipients well known to a skilled artisan in the field to which this invention belongs.

A method for preparing a botanical composition, comprises the steps of:

(i) obtaining an extract having anti-sickling activity from *Sorghum bicolor* plant material; and (ii) preparing said extract in a suitable form for treating sickle cells.

Unless defined otherwise, all technical and scientific terms used herein have the same meaning as commonly understood by one of ordinary skill in the art to which the invention belongs. The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for the intended use.

A typical procedure for extraction using *Sorghum bicolor* plant material is now set forth. *Sorghum bicolor* seeds were grown under normal green house conditions. Canadian pot mixture fortified with anhydrous ferric chloride (10 mg/pot) was used as the growth medium. Watering was done with tap water once a week. Every month the leaves were removed and air-dried. The dried leaves were extracted with aqueous sodium bicarbonate (7.4% concentration W/V at a pH ranging from about 8 to about 8.3) by stirring for about 8 hrs at normal ambient temperature. It should be noted that other buffers or extractants, neutral, organic or inorganic, at different pH could be employed to extract the anti-sickling activity from *Sorghum bicolor*. The extraction process is not limited to sodium bicarbonate or the pH range of 8.0-8.3. The method described herein is only a preferred embodiment of the extraction process. It should also be noted that the manner in which the plant is grown, including but not limited to the soil type, fertility and soil pH may also vary from the method described herein and would influence the amount of antisickling activity in the extract obtained from the plant material. The degree to which plants could vary in the accumulation of natural products that may provide medicinal, therapeutic and biological activity is well known to skilled artisans and the ability to standardize the extract to ensure pharmacologically efficacious activity by any suitable method is included in this invention, the bioassay described herein being only an example.

The extract was allowed to settle, and then decanted, filtered, centrifuged and freeze-dried.

The freeze-dried material was thoroughly blended to form a uniform mixture, which could be formulated in any suitable form, such as tablets, granules, capsules, suspensions, solutions, and the like, by well known methods. Buffers, emollients, additives, supplements, preservatives, inactive ingredients, fillers, and the like, well known to one of ordinary skill in the art to which this invention belongs, could be added to any formulation prepared by using the *Sorghum bicolor* extract.

Chemical analyses of extracts from several *Sorghum bicolor* varieties obtained from various sources were carried out using HPLC. The sickle cell bioassay was carried out by using blood removed from a sickle cell subject and exposed to the extract in vitro to measure antisickling activity employing counting and imaging techniques as described in Iyamu, et al, British Journal of Hematology, (2002), 118: 337-343.

The results shown in Table 1 indicate that *Sorghum bicolor* extract, without using plant material from any other source, has potent antisickling activity, having as much as five-fold greater anti-sickling efficacy against human sickle cells, compared to the prior art formulation disclosed in U.S. Pat. No. 5,800,819.

It should be noted that the guidance, illustrations and examples provided herein are only illustrative and not limiting, and various alternate embodiments, modifications or manipulations of the present invention would be suggested to a skilled artisan and these are included within the spirit and purview of this application and scope of the appended claims.

The invention claimed is:

1. A method of treating sickle cell disease in a subject in need thereof, comprising administering to the subject a composition comprising an extract from dried *Sorghum bicolor* leaves, without using material from any other plant, said extract having anti-sickling activity, and wherein said extract is from an aqueous sodium bicarbonate extraction in a pH range of 8 to 8.3 of dried *Sorghum bicolor* leaves.

2. The method of claim 1, wherein the composition further comprises any pharmaceutically acceptable carrier and excipients.

3. The method of claim 2, wherein said extract is formulated as a solution, suspension, powder, tablet or capsule.

4. The method of claim 1, wherein said extract comprises a solution, suspension, or powder.

5. The method of claim 1, wherein said aqueous sodium bicarbonate extract of dried *Sorghum bicolor* leaves having anti-sickling activity inhibits sickling of human red blood cells in a sickle cell bioassay and does not contain material from any other plant, wherein said extract exhibits five-fold greater anti-sickling activity than a composition disclosed in U.S. Pat. No. 5,800,819 comprising an extract of four plant materials *Piper guineenses* seeds, *Pterocarpus osun* stem, *Eugenia caryophyllum* fruit, *Sorghum bicolor* leaves, and potash.

6. The method of claim 5, wherein said four plant materials and potash contain from 12 to 17 parts by weight *Piper guineenses* seeds, from 15 to 19 parts by weight *Pterpcarpus osun* stem, from 12 to 18 parts by weight *Eugenia caryophyllum* fruit, from 25 to 32 parts by weight *Sorghum bicolor* leaves, and from 15 to 22 parts by weight potash.

7. The method of claim 1, wherein the composition is prepared in a process comprising:
  (i) obtaining an aqueous sodium bicarbonate extract in a pH range of 8 to 8.3 from dried *Sorghum bicolor* leaves, said extract having anti-sickling activity; and
  (ii) preparing said extract in a suitable form selected from tablet, granules, capsule, suspension, solution, or powder for treating sickle cell disease.

TABLE 1

COMPARATIVE RESULTS OF SICKLE CELL BIOASSAY

| Name of sample | Sample ID | Solvent used for concentration at pH 8-8.3 | Origin of *Sorghum Bicolor* seed | Sample description | Bio-Assay (% of cells still sickled) |
| --- | --- | --- | --- | --- | --- |
| *Sorghum Bicolor* | XC-214-41-IS2724 | Sod. Bi Carb | India | IS2724 1 month old leaves | 23% |
| *Sorghum Bicolor* | IS2724-4L | Sod. Bi Carb | India | IS2724 4 month old leaves | 38% |
| *Sorghum Bicolor* | IS2724-ML-5 | Sod. Bi Carb | India | IS2724 5 month old leaves | 32% |
| *Sorghum Bicolor* | IS2724-IF-4 | Sod. Bi Carb | India | IS2724 inflorescent leaves | 16% |
| *Sorghum Bicolor* | IS2724-SD-5 | Sod. Bi Carb | India | IS2724 ground seeds | 62% |
| *Sorghum Bicolor* | IS2724-ST-5 | Sod. Bi Carb | India | IS2724 stem | 63% |
| *Sorghum Bicolor* | XC-214-41-FF | Sod. Bi Carb | India | Fara Fara 1 month old leaves | 36% |
| *Sorghum Bicolor* | XC-214-41-Red | Sod. Bi Carb | India | Red Hagari 1 month old leaves | 23% |
| *Sorghum Bicolor* | PI48771-02-SD | Sod. Bi Carb | South Africa | 1 month old green leaves | 52% |
| *Sorghum Bicolor* | XC-214-38-sb4g | Sod. Bi Carb | South Africa | 4 month old green leaves | 32% |
| *Sorghum Bicolor* | XC-214-42-SA6 | Sod. Bi Carb | South Africa | 6 month old green leaves | 24% |
| *Sorghum Bicolor* | PI586787-01-SD | Sod. Bi Carb | Unknown Origin | 4 month old green leaves | 42% |
| *Sorghum Bicolor* | PI513794-01-SD | Sod. Bi Carb | Niger | 4 month old green leaves | 60% |
| *Sorghum Bicolor* | PI155889-01-SD | Sod. Bi Carb | Tanzania | 4 month old green leaves | 64% |
| *Sorghum Bicolor* | PI287617-01-SD | Sod. Bi Carb | Zimbabwe | 4 month old green leaves | 53% |
| *Sorghum Bicolor* | PI284971-01-SD | Sod. Bi Carb | Argentina | 4 month old green leaves | 51% |
| *Sorghum Bicolor* | PI810693-01-SD | Sod. Bi Carb | China | 4 month old green leaves | 54% |
| *Sorghum Bicolor* | PI585454-01-SD | Sod. Bi Carb | Ghana | 4 month old green leaves | 28% |
| *Sorghum Bicolor* | XC-214-41-Nunba | Sod. Bi Carb | Nigeria | Nunaba, 1 month old leaves | 24% |
| *Sorghum Bicolor* | XC-214-41-Nig2 | Sod. Bi Carb | Nigeria | 2 month old green leaves | 16% |
| *Sorghum Bicolor* | XC-214-41-Nig6 | Sod. Bi Carb | Nigeria | 6 month old green leaves | 26% |
| Nicosan | U.S. Pat. No. 5,800,819 | Potash | Nigeria | Nicosan from Nigeria | 88% |
| Control-Buffer | Ctr | | 500 | 0 | 97% |
| Control-Buffer | Ctr | | 500 | 0 | 98% |

8. The method of claim 7, wherein the composition is prepared in a process further comprising:
   (i) extracting dried *Sorghum bicolor* leaves with essentially 7.4% weight by volume aqueous solution of sodium bicarbonate at a pH ranging from 8.0 to 8.3 by stirring for 8 hr at ambient temperature;
   (ii) allowing the extract to settle, then decanting, filtering, centrifuging and freeze drying the resulting material; and
   (iii) thoroughly blending the freeze dried material to form a uniform mixture.

9. The method of claim 8, wherein the composition is prepared in a process further comprising
   adding a pharmaceutically acceptable carrier or excipient to said mixture; and employing said blended uniform mixture in a powder, tablet, capsule, granular or suspension form for inhibiting sickling of human red blood cells.

\* \* \* \* \*